US00PP09816P

United States Patent [19]

VandenBerg

[11] Patent Number: Plant 9,816

[45] Date of Patent: Mar. 4, 1997

[54] CHRYSANTHEMUM PLANT NAMED 'FIDELIO'

[75] Inventor: Cornelis P. VandenBerg, Salinas, Calif.

[73] Assignee: Yoder Brothers, Inc., Barberton, Ohio

[21] Appl. No.: 616,653

[22] Filed: Mar. 15, 1996

[51] Int. Cl.[6] ..... A01H 5/00

[52] U.S. Cl. ..... Plt./77

[58] Field of Search ..... Plt./77

*Primary Examiner*—Howard J. Locker
*Attorney, Agent, or Firm*—Foley & Lardner

[57] ABSTRACT

A Chrysanthemum plant named Fidelio particularly characterized by its flat incurved capitulum form; decorative capitulum type; white ray floret color; diameter across face of capitulum of 70 to 86 mm when fully opened; flowering response in Salinas under normal temperatures is 49 to 52 days after start of short days. Flowering response in Bogota, Columbia is 62 to 69 days after start of short days; plant height is 91 to 104 cm when grown in Salinas with 11 to 13 long days prior to start of short days; height is 104 to 122 cm when grown in Bogota, Colombia with 14 to 15 long days prior to start of short days; peduncle length of the first and the fourth laterals at flowering after removing the apical bud is 8 to 10 cm and 13 to 18 cm when grown in Salinas; peduncle length when grown in Bogota, Colombia is 10 to 15 cm and 15 to 23 cm, respectively; production of 9 to 10 laterals, each producing one terminal flower when grown in Salinas; production is 7 to 9 laterals when grown in Bogota, Colombia; and uniform flowering in year round flowerings.

3 Drawing Sheets

The present invention comprises a new and distinct cultivar of Chrysanthemum, botanically known as *Dendranthema grandiflora,* and referred to by the cultivar name Fidelio.

Fidelio, identified as 0960 (90-974005), was originated from a cross made by Cornelis P. VandenBerg in a controlled breeding program in Salinas, Calif., in November of 1989.

The female parent of Fidelio was an unnamed seedling, identified as 1123 (85-247002) and described as a flat decorative cut mum with a white ray floret color. The female parent was discarded from all programs in October of 1991.

The male parent of Fidelio was an unnamed seedling, identified as 1359 (85-271002) and described as a white decorative cut mum with many disc florets.

Fidelio was discovered and selected as one flowering plant within the progeny of the stated cross by Cornelis P. VandenBerg in February 1991, in a controlled environment in Salinas, Calif.

The first act of asexual reproduction of Fidelio was accomplished when vegetative cuttings were taken from the initial selection in May of 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Fidelio are firmly fixed and are retained through successive generations of asexual reproduction. Fidelio has not been observed under all possible environmental conditions. The phenotype may vary significantly with variations in environment such as temperature, light intensity and daylength, without, however, any variance in genotype.

The following observations, measurements and comparisions describe plants grown in Salinas, Calif., and near Bogota, Columbia, South America under greenhouse conditions which approximate those generally used in commercial greenhouse practice.

The following traits have been repeatedly observed and are determined to be basic characteristics of Fidelio, which, in combination, distinguish this Chrysanthemum as a new and distinct cultivar:

1. Flat incurved capitulum form.
2. Decorative capitulum type.

3. White ray floret color.
4. Diameter across face of capitulum of 70 to 86 mm when fully opened.
5. Flowering response in Salinas under normal temperatures is 49 to 52 days after start of short days. Flowering response in Bogota, Colombia is 62 to 69 days after start of short days.
6. Plant height is 91 to 104 cm when grown in Salinas with 11 to 13 long days prior to start of short days; height is 104 to 122 cm when grown in Bogota, Colombia with 14 to 15 long days prior to start of short days.
7. Peduncle length of the first and the fourth laterals at flowering after removing the apical bud is 8 to 10 cm and 13 to 18 cm when grown in Salinas; peduncle length when grown in Bogota, Colombia is 10 to 15 cm and 15 to 23 cm, respectively.
8. Production of 9 to 10 laterals, each producing one terminal flower when grown in Salinas. Production is 7 to 9 laterals when grown in Bogota, Colombia.
9. Uniform flowering in year round flowerings.

The accompanying photographic drawings show typical inflorescence and leaf characteristics of Fidelio, with the colors being as nearly true as possible with illustrations of this type.

Sheet 1 is a color photograph of Fidelio grown as a single stem spray cut mum.

Sheet 2 is a black and white photograph of three views of the inflorescence of Fidelio.

Sheet 3 is a black and white photograph showing the upper and under sides of the leaves of Fidelio at 3 stages of development (mature, intermediate and immature).

In sheets 2 and 3 a measuring tape in centimeters has been added.

Of the commercial cultivars known to the inventor, the most similar in comparison to Fidelio is the unpatented but well known cultivar Polaris. Reference is made to attached Chart A, which compares certain characteristics of Fidelio with the same characteristics of Polaris. Similar traits are capitulum form and type. The ray floret color of Fidelio and Polaris is comparable, with Fidelio having a white ray floret color, while the ray floret of Polaris is described as creamy white. When compared with Polaris, Fidelio has in general a smaller diameter of capitulum, but a wider range of flower size, an earlier flowering response, a slightly shorter plant height and shorter peduncles than Polaris.

In the following description color references are made to the Royal Horticultural Society Colour Chart. The color values were determined on plant material grown as a single stem spray cut mum in Salinas, Calif. on May 24, 1995.

Classification:

*Botanical.*—*Dendranthema grandiflora* cv Fidelio.

*Commerical.*—Flat decorative spray cut mum.

INFLORESCENCE

A. Capitulum:

*Form.*—Flat.

*Type.*—Decorative.

*Diameter across face.*—70 to 86 mm when fully opened.

B. Corolla of ray florets:

*Color (general tonality from a distance of three meters).*—White.

*Color (upper surface).*—155D.

*Color (under surface).*—155D.

*Shape.*—Cross-section concave, longitudinal section straight, rounded ray floret tips.

C. Corolla of disc florets:

*Color (mature).*—Closest to 14B.

*Color (immature).*—Closest to 149D.

D. Reproductive organs:

*Androecium.*—Present on disc florets only; scant to no pollen.

*Gynoecium.*—Present on both ray and disc florets.

PLANT

A. General appearance:

*Height.*—is 91 to 104 cm when grown in Salinas with 11 to 13 long days prior to start of short days; height is 104 to 122 cm when grown in Bogota, Colombia with 14 to 15 long days prior to start of short days.

B. Foliage:

*Color (upper surface).*—147A.

*Color (under surface).*—147B.

*Shape.*—Deeply lobed, serrated.

CHART A

COMPARISON OF FIDELO AND POLARIS

| CHARACTERISTICS | FIDELIO | POLARIS |
|---|---|---|
| Ray floret color | White | Creamy white |
| Captitulum form and type | Flat decorative | Flat decorative |
| Diameter across face of capitulum | 70 to 86 mm | 76 to 83 mm |
| Flowering response | | |
| in Salinas | 49 to 52 days | 51 to 53 days |
| in Bogota | 62 to 69 days | 69 to 73 days |
| Plant height | | |
| 11–13 long days Salinas | 91 to 104 cm | 94 to 113 cm |
| 14–15 long days Bogota | 104 to 122 cm | 107 to 127 cm |
| Peduncle length | | |
| 1st lateral Salinas | 8 to 10 cm | 14 to 15 cm |
| 4th lateral Salinas | 13 to 18 cm | 18 to 20 cm |
| 1st lateral Bogota | 10 to 15 cm | 15 to 18 cm |
| 4th lateral Bogota | 15 to 23 cm | 20 to 23 cm |

COMPARISONS MADE OF PLANTS GROWN AS SINGLE STEM SPRAY CUT MUMS IN SALINAS, CALIFORNIA AND IN BOGOTA, COLOMBIA

What is claimed is:

1. A new and distinct Chrysanthemum plant named Fidelio, as described and illustrated.

* * * * *

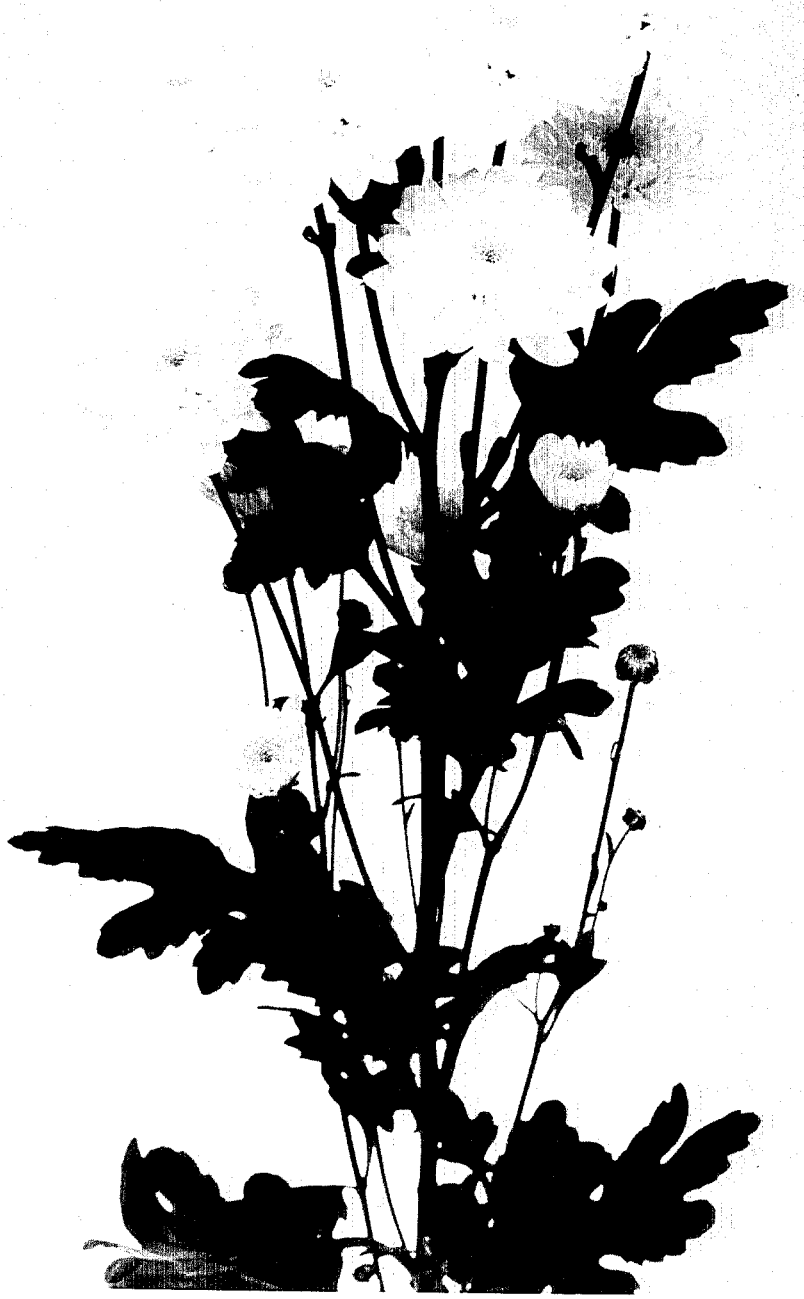

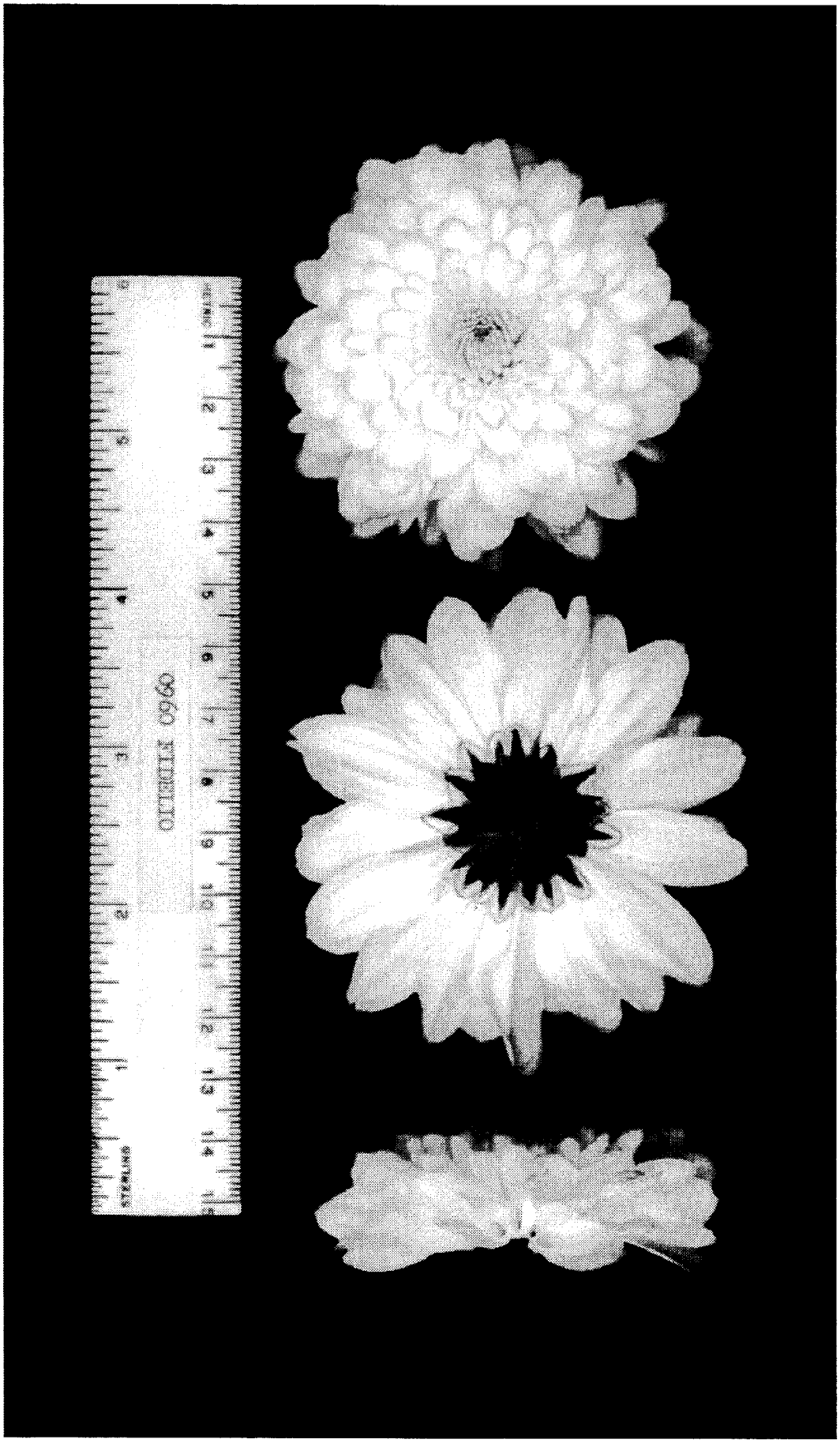
STAEDTLER
STILOMETRO 961G

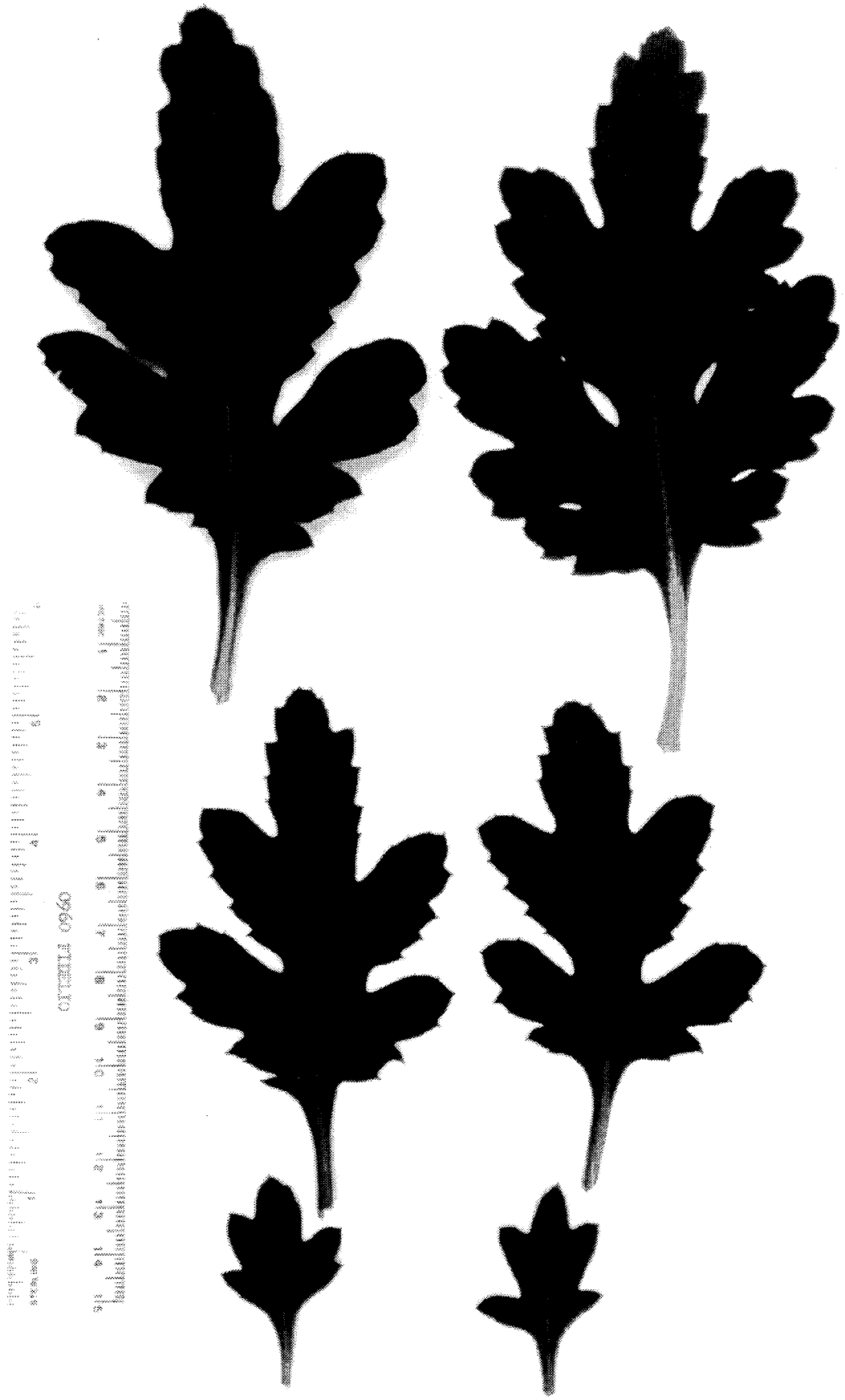
OCTELLO
0960